United States Patent [19]

Folestad et al.

[11] Patent Number: 4,548,498
[45] Date of Patent: Oct. 22, 1985

[54] LASER INDUCED FLUORESCENCE DETECTION IN MODERN LIQUID CHROMATOGRAPHY WITH CONVENTIONAL AND MICRO COLUMNS

[76] Inventors: Sven S. Folestad, Krukmakaregatan 1 C, S-414 60 Göteborg; Bo G. Galle, Norska gatan 32, S-417 22 Göteborg; Lars Göran I. Johnson, S.Viktoriagatan 52, S-411 30 Göteborg; Björn O. Josefsson, Vaktmästaregången 16, S-413 18 Göteborg, all of Sweden

[21] Appl. No.: 457,070
[22] PCT Filed: May 4, 1982
[86] PCT No.: PCT/SE82/00147
§ 371 Date: Jan. 3, 1983
§ 102(e) Date: Jan. 3, 1983
[87] PCT Pub. No.: WO82/03918
PCT Pub. Date: Nov. 11, 1982

[30] Foreign Application Priority Data

May 4, 1981 [SE] Sweden ............... 8102772

[51] Int. Cl.[4] .............. G01N 21/64; G01N 21/85
[52] U.S. Cl. .................. 356/318; 250/458.1
[58] Field of Search ............. 356/72, 73, 317, 318, 356/343, 410; 250/458.1, 459.1, 461.1, 461.2, 574

[56] References Cited

U.S. PATENT DOCUMENTS

| | | | |
|---|---|---|---|
| 3,669,542 | 6/1972 | Capellard | 250/574 |
| 3,715,771 | 12/1972 | Friedman et al. | 356/343 |
| 4,008,397 | 2/1977 | Zorodowski | 250/461.1 |
| 4,181,853 | 1/1980 | Abu-Shumays et al. | 250/461.1 |
| 4,199,686 | 4/1980 | Brunsting et al. | 250/459.1 |
| 4,243,318 | 1/1981 | Stöhr | 356/318 |
| 4,273,443 | 6/1981 | Hogg | 356/344 |

Primary Examiner—F. L. Evans
Assistant Examiner—S. A. Turner

[57] ABSTRACT

In a method and a device for laser induced fluorescence detection in liquid chromatography a light beam (1) is directed from a laser source (2) towards a liquid flowing in a chosen flow direction for the detection of the presence of one or several substances. At a flow point illuminated by the light beam (1) the liquid is brought to emit a fluorescence radiation (3) which is received by a receiving unit (6). The light beam (1) is directed substantially perpendicularly to the flow direction of the liquid. The liquid is brought to pass the illuminated flow point in the form of a column with an accurately defined surface. The fluorescence radiation (3) is received in a direction which deviates from directions emanating from the illuminated flow point perpendicularly from the flow direction of the liquid column.

11 Claims, 9 Drawing Figures

LASER INDUCED FLUORESCENCE DETECTION IN MODERN LIQUID CHROMATOGRAPHY WITH CONVENTIONAL AND MICRO COLUMNS

BACKGROUND OF THE INVENTION

Extra column band broadening in detectors has been paid attention to since high performance liquid chromatography (HPLC) was introduced. Accordingly, as columns and injectors have been improved the requirement on detector performance has increased to minimize peak broadening by dispersion. In this respect the cell volume as well as connections play an important role. The whole detector arrangement may influence the flow properties which in turn affect the band spreading.

There is a growing interest in the use of miniaturized HPLC systems based on packed microbore columns or open tubular columns. These chromatographic systems may exhibit high resolving power together with a low flow rate of the mobile phase. The microbore packed column technique was introduced by Scott and Kucera [1,2] (for these and other references indicated in brackets please refer to list at end of the specification). They pointed out the importance of diminishing the detector cell volume to utilize the separation effiency of the column. Ishii et al [3,4] constructed a miniaturized HPLC system with open tubular columns which have essentially smaller inner diameters of about 50 $\mu$m. With this technique the detector cell requires still smaller volumes, in the range of 0.1-1 $\mu$l. Knox and Gilbert [5] calculated that the effective detection volumes should be in the order of 1-10 nl before there is any hope of operating capillary HPLC systems under optimal conditions. They also stated that the practical limitation to capillary HPLC arises from the dispersion by the detector.

When considering different small volume detectors the fluorescence technique is promising because of its high sensitivity. HPLC fluorescence detectors utilizing laser excitation radiation have recently been introduced [6, 7, 8]. Laser fluorimetry has some important characteristics which may be advantageous with small volume detectors. The produced emission radiation is directly proportional to the intense laser excitation light which leads to extreme sensitivity. Another property is the spatial coherence of the laser beam which facilitates the irradiation of small detector volumes. In addition the monochromaticity of the laser makes it easier to suppress scattered light from Rayleigh and Raman processes as well as reflexions without sacrificing sensitivity.

Diebold and Zare [6] presented a windowless flow cell where the HPLC effluents flow from a steel capillary tube down to a rod 2 mm below forming a droplet bridge of 4 $\mu$l volume. Focusing the laser beam to a small spot inside the droplet facilitates rejecting the elastically scattered light. With a pulsed HeCd laser and the use of gated detection electronics they achieved very high sensitivity when determining aflatoxins. Hershberger et al. [7] designed a HPLC cell based on the sheath flow principle where the affluent is injected in the center of an ensheathing solvent stream under laminar flow conditions. The laser beam enlighted cell volume is very small or in the range of 6-150 nl. Since the windows are not in contact with the sample flow the stray light from the windows is reduced. Sepaniak and Yeung [8] used a quartz capillary tube where the HPLC effluent moved upwards. A focused laser beam was placed in the effluent underneath an optical fiber. The emitted light was collected through the fiber perpendicular to the laser beam. The construction leads to a minimal influence of scattered and fluorescent light from the capillary tube walls. The limiting factors of fluorescence detectability are to a great part connected with background noise from the cell, optical components, solvent and sample contaminants. The reduction of the background emission is highly dependent on the detector cell design. The objective of this invention is to design a laser based detector ideal to use with conventional HPLC columns as well as microbore columns. Special attention has been paid to the effective cell volume regarding extra column effects by comparing the efficiency of the two systems.

BRIEF DESCRIPTION OF THE DRAWING

The invention is illustrated, by way of example, in the accompanying drawings, in which.

DETAILED DESCRIPTION OF THE PREFERRED EMBODIMENT

Figure 1:
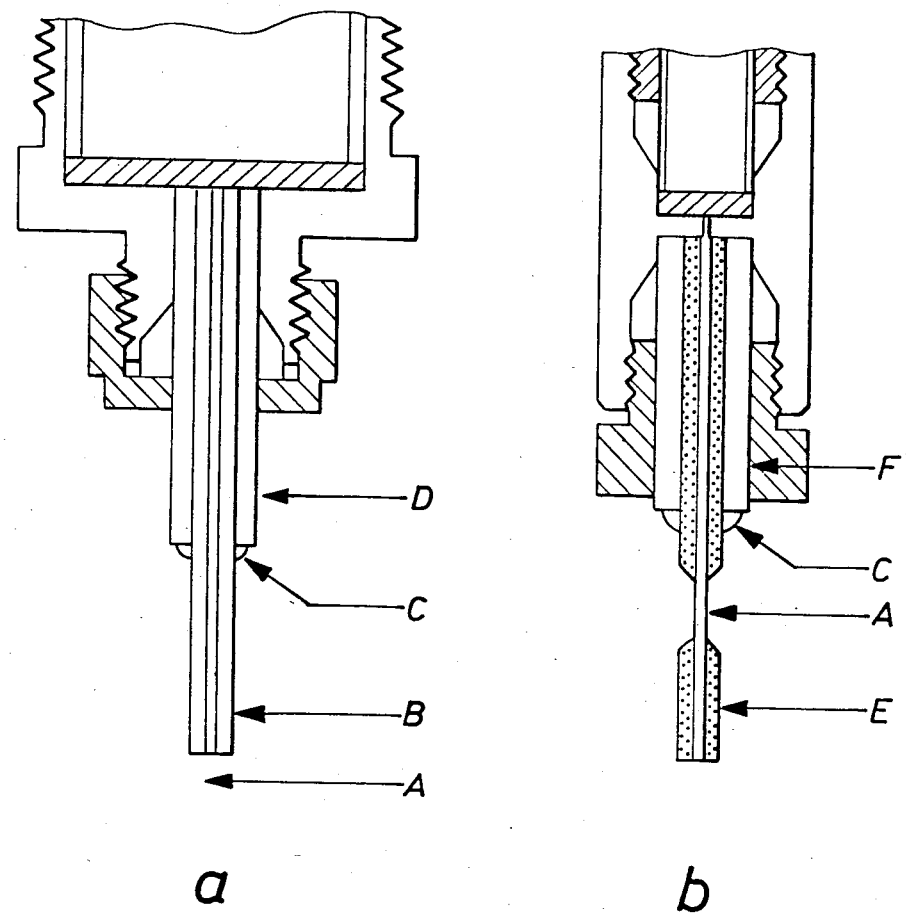
FIG. 1 shows a schematic diagram of detector cell arrangements, namely, (a) free falling jet, and (b) a microbore column quartz capillary.

FIG. 1 shows a schematic diagram of detector cell arrangements, namely (a) free falling jet, (b) microbore column quartz capillary. In this figure, A is a laser focusing point; B a syringe needle SGE, 17 mm, ID 0.12 mm, OD 0.5 mm. C is a cyanoacrylate adhesive. D is SS tubing 1/16", 15 mm, ID 0.2 mm. E is a fused silica capillary, 60 mm, ID 0.20 mm, OD 0.30 mm. F is SS tubing 1/16", 17 mm, ID 0.35 mm.

Figure 2:
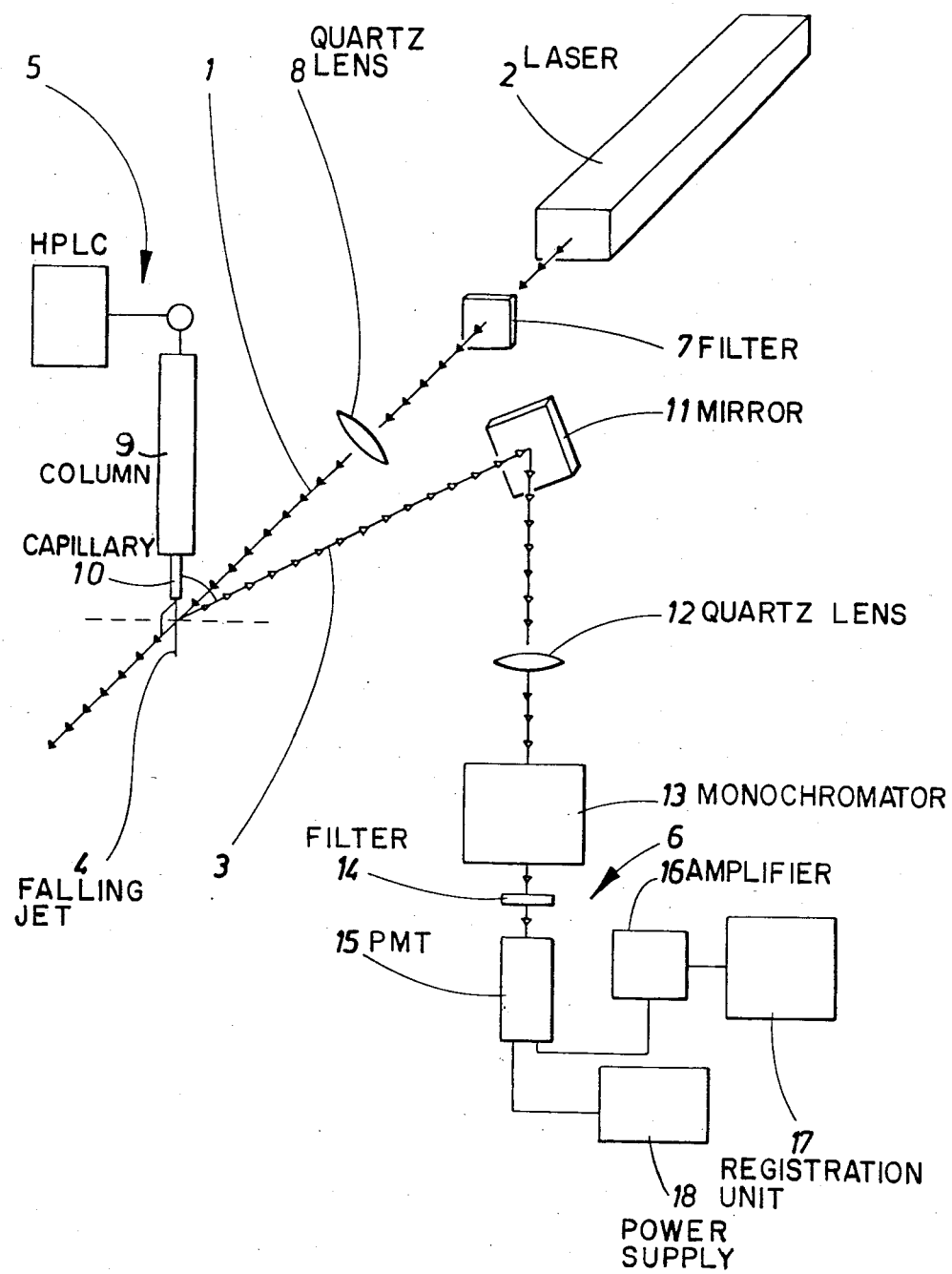
FIG. 2 shows a schematic diagram of the experimental instrumentation arrangement.

FIG. 2 shows a schematic diagram of the experimental instrumentation arrangement.

Figure 3:
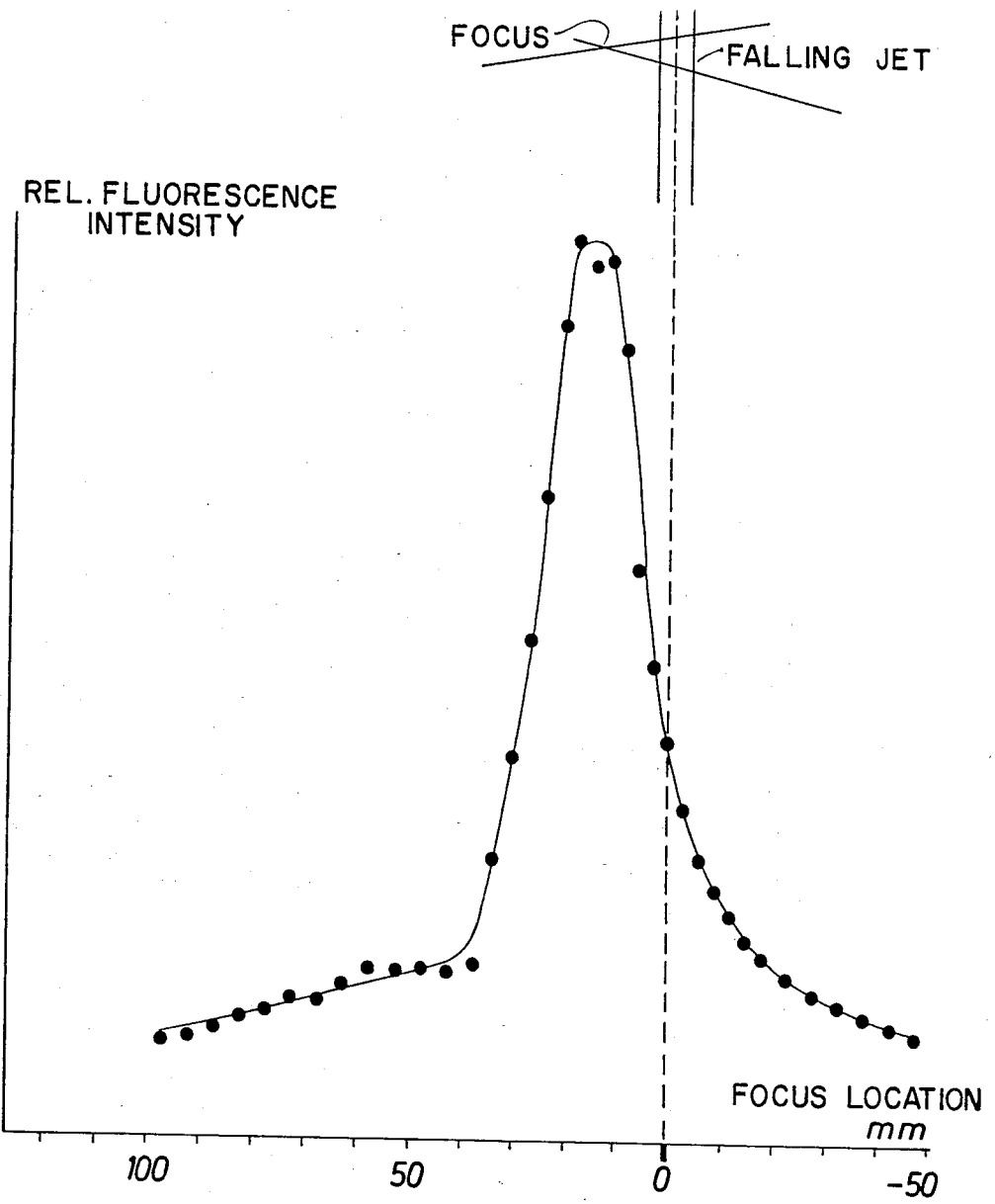
FIG. 3 shows the relative fluorescence intensity versus focus location on the falling jet.

FIG. 3 shows the relative fluorescence intensity versus focus location on the falling jet (OD 0.3 mm). Maximum response is found 15 mm ahead of the jet. Column Nucleosil 7.5 $\mu$m, mobile phase hexane containing fluoranthene, flow rate 2 ml/min.

Figure 4:
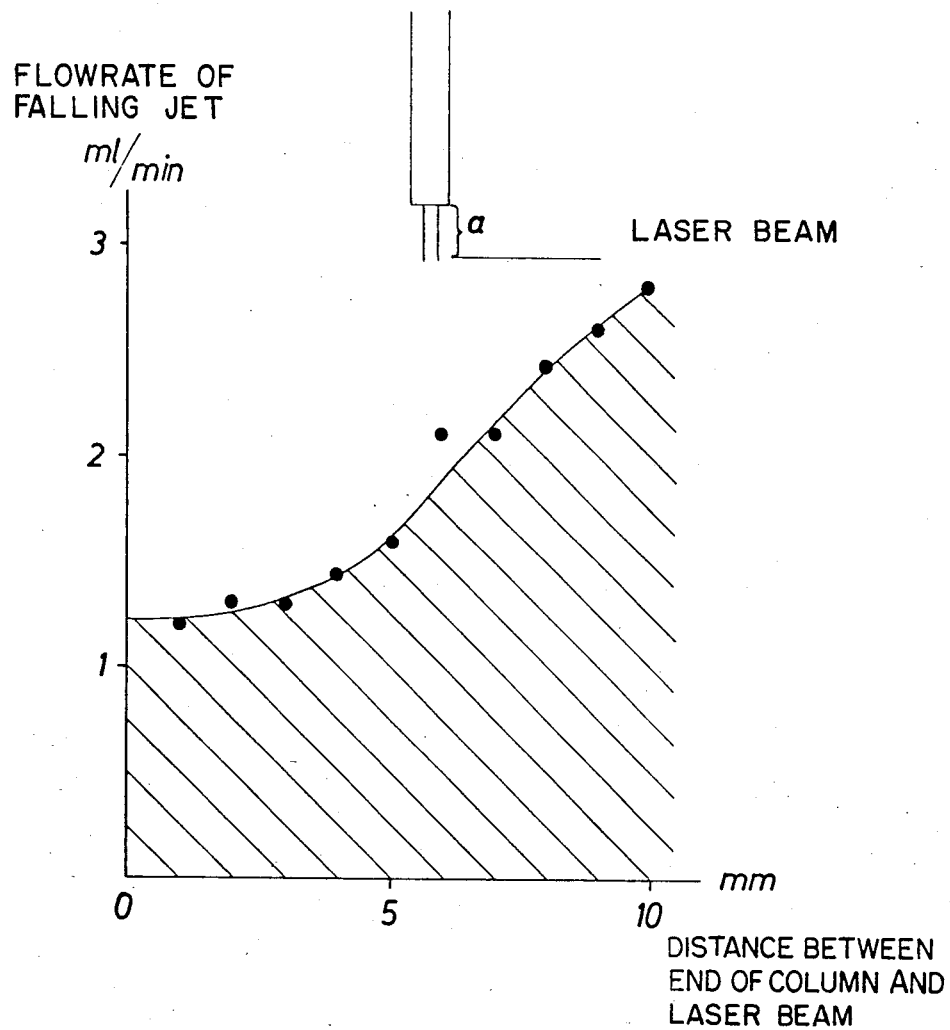
FIG. 4 shows stability of the falling jet with hexane as mobile phase.

FIG. 4 shows stability of the falling jet with hexane as mobile phase. Drop formation occurs in the shaded area. The flow rate is plotted against the distance between the column effluent exit and the laser excitation point.

Figure 5:
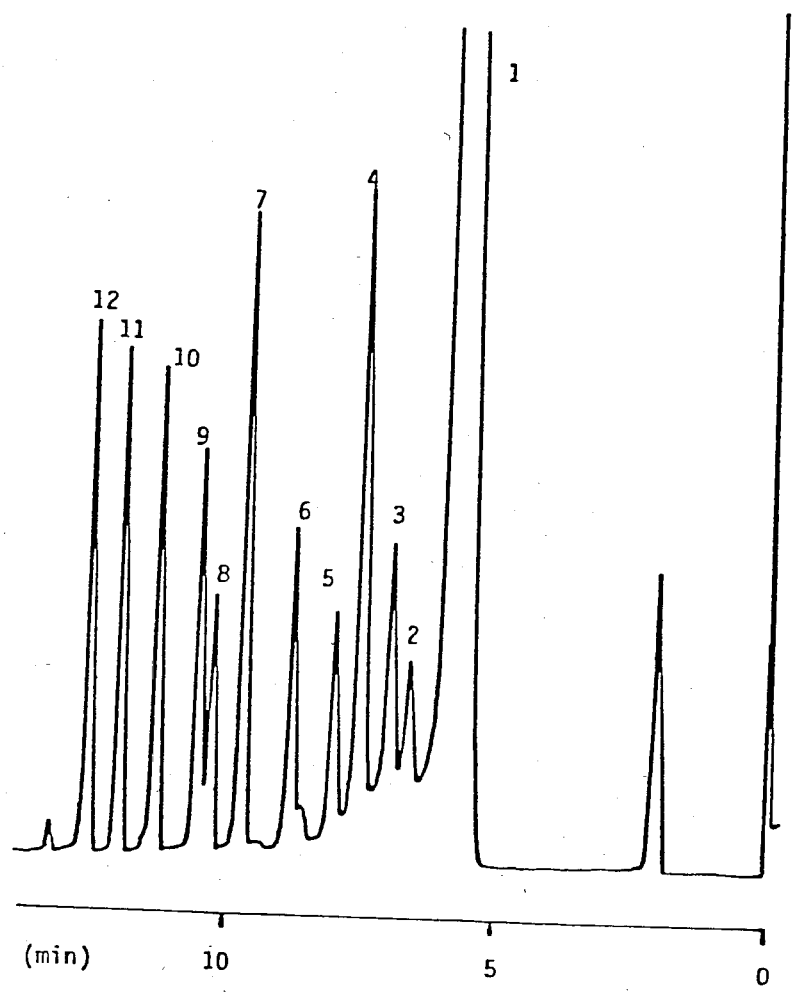
FIG. 5 shows separation of a standard mixture of 11 Dns-hydrazones.

FIG. 5 shows separation of a standard mixture of 11 Dns-hydrazones. The column is 200×4.6 mm, Nucleosil RP-18 5 $\mu$m. Mobile phase, methanol:water, linear gradient 50 to 100% in 12 min. Flow rate 1.3 ml/min. 10 μl injected and 1=Dns-hydrazine, 2=Formaldehyde, 3=Acetaldehyde, 4=Acetone, 5=Propanal, 6=Butanal, 7=Pentanal, 8=Benzaldehyde, 9=Hexanal, 10=Heptanal, 11=Octanal, 12=Nonanal.

Figure 6:
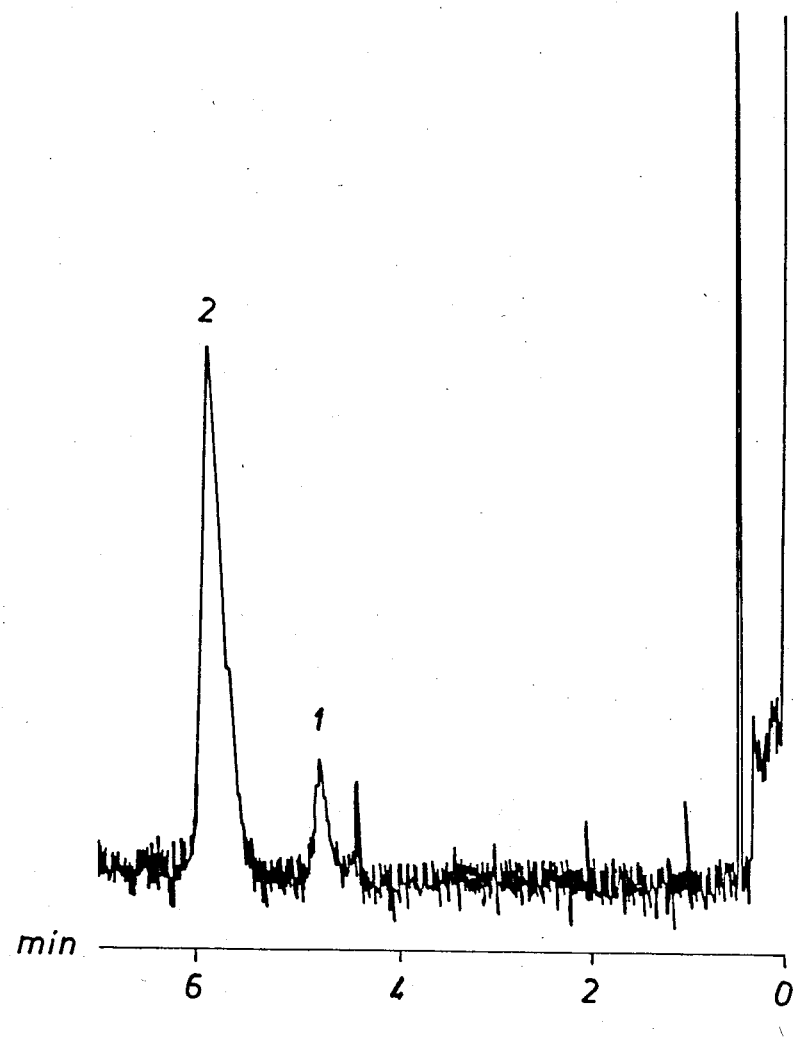
FIG. 6 shows the minimum detectable quantity of fluoranthene.

FIG. 6 shows the minimum detectable quantity of fluoranthene. The column is 200×4.6 mm, Nucleosil 7.5 μm, mobile phase hexane. Flow rate 2 ml/min. Injected volume 10 μl. 1=Anthracene, 2-Fluoranthene 20 fg.

Figure 7:
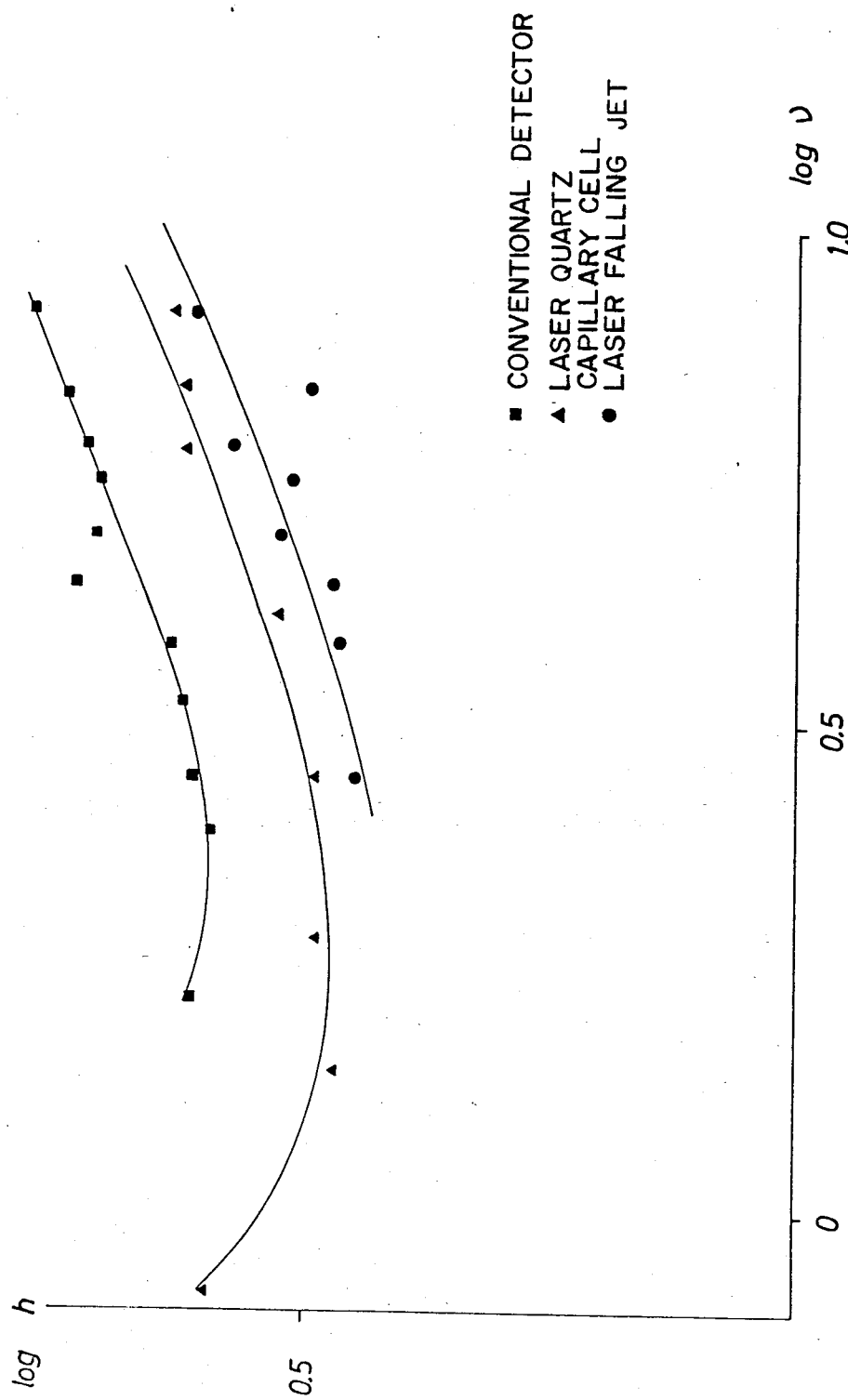
FIG. 7 shows log h versus log $\nu$ for conventional HPLC with different detectors.

FIG. 7 shows the plot of log h versus log ν for conventional HPLC with different detectors. Column 150×4.6 mm, Nucleosil 7.5 μm, mobile phase hexane:-methylene chloride 5%. Solution anthracene.

Figure 8:
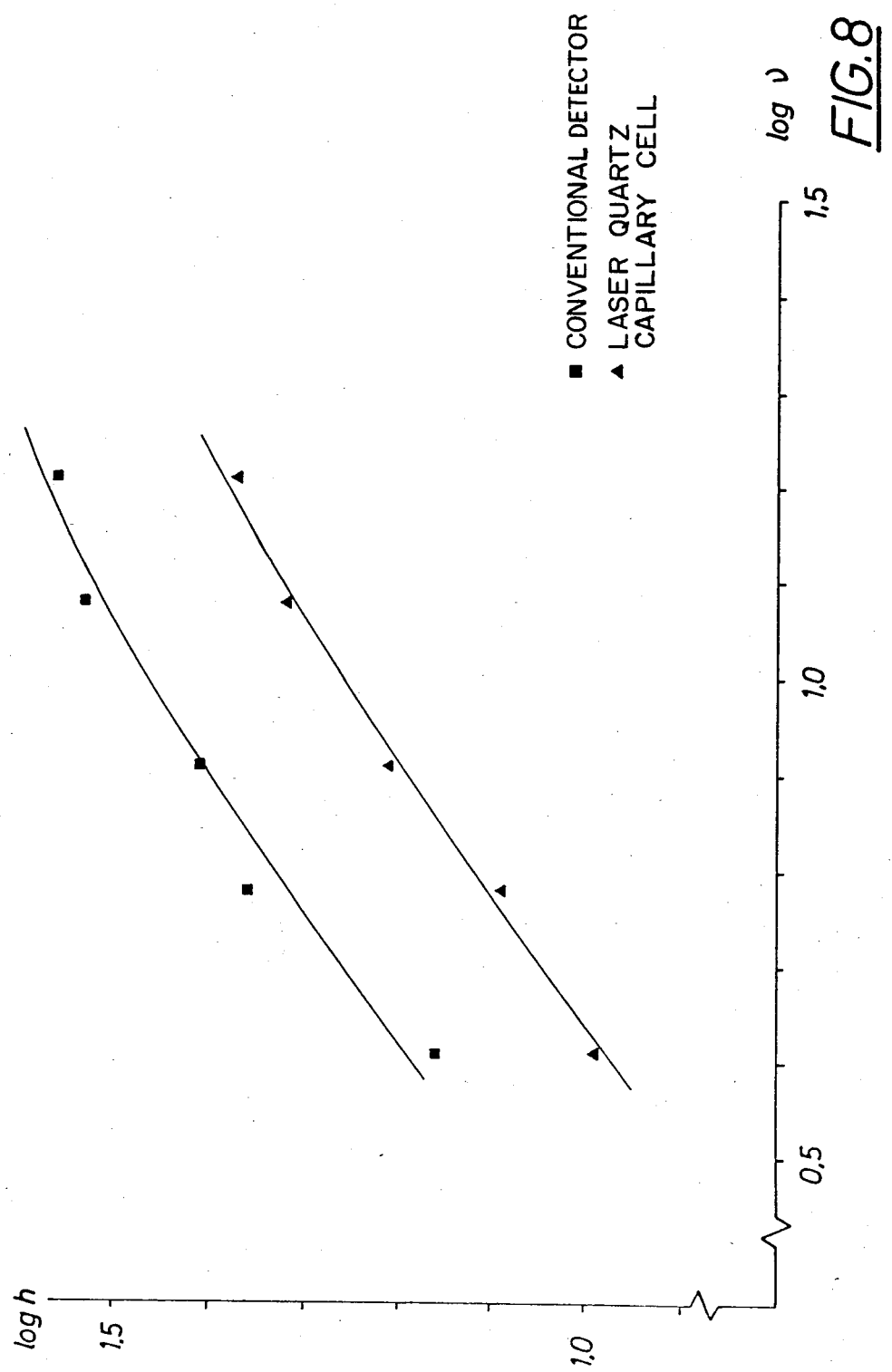
FIG. 8 shows log h versus log $\nu$ for microbore column with different detectors.

FIG. 8 shows the plot of log h versus log ν for microbore column with different detectors. Column 400×1.0 mm, Nucleosil 7.5 μm, mobile phase hexane:-methylene chloride 5%. Solution anthracene.

EQUIPMENT

Conventional HPLC system

An LDC chromatographic system consisting of two Constametric III pumps and a Gradient Master was used. Injections were made with a Valco injector with a 10 μl loop. Separations were performed on a 150 mm×4.6 mm column packed with Nucleosil 7.5 μm Silica and on a 200 mm×4.6 mm Nucleosil 5 μm RP18 column. The columns were mounted in a rack and pinion arrangement which allowed vertical adjustment. Hexane, methanol and methylenechloride solvents from Rathburn Chemicals (HPLC grade) and double distilled water were used in different mobile phase compositions.

For comparative studies an FS 970 LC Fluorimeter from Schoeffel Instruments were used, equipped with a Corning 7-54 primary filter and a 418 nm cut off secondary filter. The excitation wavelength was set to 360 nm.

Microbore HPLC system

The low flow-rates were maintained with a Waters M-6000 A pump. The frequency generator of the pump was disconnected and replaced by a Tektronix FG 502 Function Generator. Samples were injected with a Valco air actuated valve having a fixed sample volume of 0.5 μl. Columns were constructed from 10 and 20 cm lengths of 1/16" OD, 1 mm ID SS tubing. Nucleosil 7.5 μm Silica particles were suspended in methanol and pumped into the columns at a pressure of 600 bar using a Haskel DST 150 air driven fluid pump. Acetone, methylenechloride and the appropriate effluent composition were used for conditioning purposes.

Laser detectors

Free Falling jet

The effluent from the conventional HPLC columns was arranged by means of a free falling thin jet. The jet stream was produced by a small bore capillary which is shown in FIG. 1. A short piece of a SGE syringe needle, OD 0.5 mm and ID 0.12 mm, is inserted in a 1/16" SS tubing ID 0.2 mm, drilled out to fit the syringe needle. The needle is fixed with cyanoacrylate adhesive. The capillary was then connected to the column end. The construction gives a very fine jet of the column effluent at flow-rates down to approximately 1 ml/min.

Quartz capillary tube

An alternative detector design to the falling jet was required at flow-rates below 1 ml/min. Different quartz capillary tubes were tested for flow rates typical of miniaturized HPLC systems. It was found that fused silica capillary ID 0.2 mm and OD 0.3 mm from Hewlett Packard commonly used as GC/GC columns yielded lowest fluorescence background. The capillary was mounted to the column end inside a steel capillary tube as shown in FIG. 1. The polyimide coating on the fused silica capillary was carefully burnt off on a distance of 5 mm just below the end of the SS tubing using a gas flame. The uncovered area was then washed with methylenechloride. The laser beam is focused on the uncovered part of the capillary. The capillary tube allows any flow rate commonly used in conventional as well as microbore HPLC.

Optical arrangements

In FIG. 2 a schematic view of the optical system is outlined. As excitation source the monocromatic output from a Coherent Radiation CR 3000 K Krypton ion CW laser run in the UV-mode was used. This laser emits radiation at 351 and 356 nm with a total effect of 1–2 W. After suppressing the bluish fluorescence light, emanating from the laser cavity by means of a bandpass color filter UG1, the laser beam was focused with a quarts lens onto the detector cell underneath the column. Due to circumstances out of applicants' control different lenses were used with focal lengths ranging from 15 to 60 cm. In order to avoid the strong scattered light in the horizontal plane emanating from the cylindrical surface of the vertically mounted detector cell, detection was achieved at an angle of approximately 30° to this plane. After reflexion in a front surface mirror the fluorescence light is collected and focused onto the entrance slit of a Jobin Yvon HL monochromator using a quartz lens ($f=15, \phi=10$). Depending on the nature of the experiment the entrance slit was varied between 1–6 mm, while the exit slit was fixed at 17 mm yielding a bandpass of 28 nm. For convenience the monochromator was centered at 450 nm during all experiments. A compromise was made between maximum fluorescence yield and rejection of the Raman peak of water and hexane as well as elastically scattered light. The elastically scattered light was further suppressed with a cut-off filter WG 385 or GG 420 before reaching the photomultiplier-tube (EMI 9558 QB). The output of the PMT is then, after amplification, fed to a stripchart recorder. All experiments were performed under dark room conditions.

Procedure and results

Detection by means of the free falling jet

Investigations were carried out to find the maximum signal response by varying the focusing point of the laser beam vis-a-vis the falling jet. Different distances between the lens and the jet were tested at which the focus was located in front of, inside and behind the jet. The results are shown in FIG. 3. The experiment was facilitated by pumping a hexane solution containing a constant concentration of fluoranthene as marker. The maximum response was expected to be symmetrical around the distance corresponding to the focal length of the lens. However, maximum response was found when the laser beam was focused 15 mm ahead of the falling jet, corresponding to a laser beam diameter comparable to the diameter of the jet. No other maxima were found. One possible explanation of this discrepancy is that the distance from the lens to the true focus is not identical with the lens focal length. This effect may be due to the divergence of the laser and imperfections in the optical components. Scanning the laser beam horizontally, maximum response was achieved when the laser beam was in the center of the jet. At maximum response an intense disc of reflected light appeared in the plane perpendicular to the jet stream.

The optical properties of the jet are dependent on e.g. flow rates, solvent properties and diameter of the capillary. With the capillary diameter of 0.12 mm different flow rates were run to establish the minimum flow without turbulence. As shown in FIG. 4 the hexane as mobile phase could be used down to a flow of 1.2 ml/min. For gradient runs (methanol:water 0 to 100% in 10 min.) an unaffected baseline was achieved at a flow rate of 1.5 ml/min. Droplet formation appeared at a flow rate of 1.0 ml/min when water content was approximately 55%. An example of a gradient run is shown in FIG. 5.

A brief test of how the signal depended upon varying the effect of the laser resulted in that no saturation could be observed.

Quartz capillary cell

The laser beam was focused directly on the quartz capillary in the same way as with the falling jet. The background noise increased six times. However, the signal increased with the same factor, thus the signal to noise ratio remained constant. The increased signal may be a result of a more favorable geometry of the quartz capillary tube which results in multiple internal reflexions.

Detection limit

Under the conditions used for the falling jet, the minimum detection limit was established. FIG. 6 shows a chromatogram of an injected sample containing 20 fg fluoranthene ($20 \times 10^{-15}$ g in 10 µl hexane). The capacity value was 3.2 and the signal to noise ratio was 13. The linear flow through the quartz capillary detector was about 300 cm/s. Since the laser excitation volume is about 1 nl there are very few molecules present in the measured volume.

Applications

There are a limited number of compounds which emit fluorescent light. Furthermore they should be excited at the laser wavelengths available. Partly these restrictions may be overcome by using the fluorescence labeling technique [9]. A chromatogram of 11 Dns-hydrazone derivatives of carbonyl compounds is shown in FIG. 5. The laser free falling jet detector was used to illustrate a gradient elution application.

Comparison of different detector systems coupled to a conventional HPLC column A conventional fluorescence detector as well as the two different laser detectors were coupled to an HPLC column. The column system and the separation conditions were the same in the three experiments. Thus the cell arrangements could be compared according to band broadening on the detector side. The HETP curves for the three cases are shown in FIG. 7. The respective detector dead volumes were: Schoeffel detector approximately 5 µl; the falling jet 0.6 µl and the quartz capillary 1.0 µl. The illuminated volume with the two laser detectors was about 1 nl. Thus the differences in the HETP curve are mainly derived from the connections.

The band broadening in the capillary connection tubes was calculated from the formula by Taylor [10] which is valid under conditions of laminar flow. The falling jet variance was $\delta^2 = 1.49$ µl$^2$ and the quartz capillary yielded $\delta^2 = 2.84$ µl$^2$ at the flow rate of 1.5 ml/min. These band broadening contributions are very small compared to the total dispersion in the connection tubings.

Comparison of different detectors coupled to a microbore column

The quartz capillary detector cell was tested with a micro bore column. A comparison under same conditions was made with a conventional HPLC fluorescence detector with a relatively small detector cell dead volume. The HETP curve is shown in FIG. 8. In the experiment the pump flow rates were in the range 100 to 400 µl/min.

Discussion

In a recently published review Yeung and Sepaniak [11] discussed the potential to use laser fluorimetric detection in HPLC. The previously reported laser based detectors are characterized by complicated constructions e.g. to suppress straylight. Furthermore the detectors are not designed to be used with a miniaturized system or gradient elution. The only detector that may be used with gradient operation, is the cell based on an optical fiber inside a quartz tube cell (20 µl cell volume). However, this detector is difficult to make smaller without concomitant decrease in sensitivity. The free falling jet principle is a straightforward approach and it has been practised in turbidimeters to measure scattered light from particles. The jet is characterized by stability and a well defined smooth surface also during gradient elution with flow rates typically of conventional HPLC columns. The background is easy to suppress with the collecting optics out of the perpendicular plane to the jet stream. Actually a 30° angle results in a background signal decrease of 6 magnitudes. This arrangement yields the highest sensitivity or a detection capacity is the fg-level. When using laser excitation with its well defined beam it is far easier to manipulate the optics than to complicate the construction of the flow cell.

The use of quartz capillaries as flow cells in fluorescence is very common. The most critical factor with quartz materials is the background fluorescence. Compared to the falling jet cell the quartz capillary flow cell has only one advantage, namely that low flow rates are possible which in turn is necessary for HPLC-systems.

As mentioned in the introduction one main advantage of laser excitation is the possibility to irradiate small detector volumes. Therefore laser based detectors may be successful with miniaturized systems. Hershberger et al. [7] reported the possibility to use a detector volume down to 1 nl. This is true for the laser irradiated volume in their detector, however, by no means for the whole detector volume including the connections.

Figure 9:
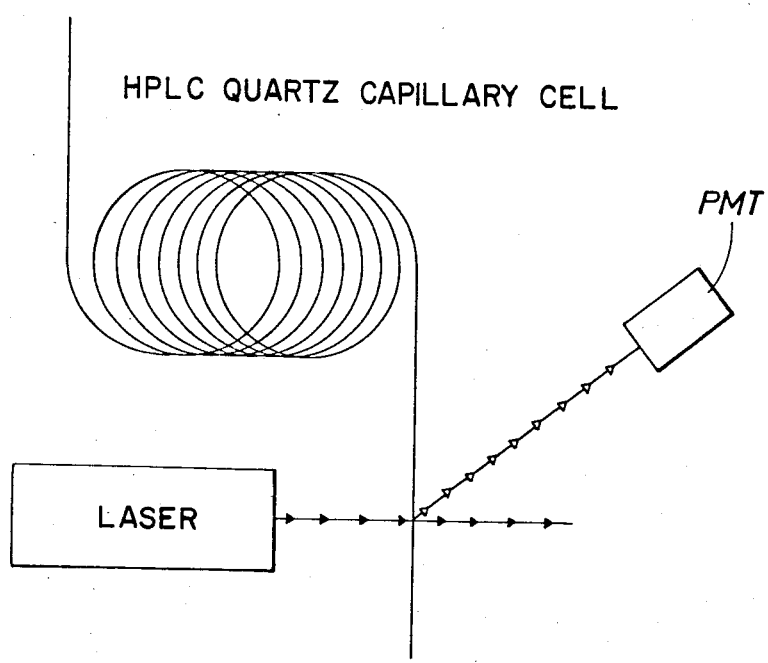
FIG. 9 shows schematic view of laser inducing fluorescence detection directly on a HPLC quartz capillary column.

Miniaturized HPLC systems are characterized by narrow peaks. The peaks should not be dispersed anywhere in the detector system. Conventional detectors with dead volumes of 5 µl are not feasible to use without an additional make-up liquid to sweep the detector [12, 13]. The decrease of sensitivity by dilution effects may be partly compensated by laser excitation, however, this does not constitute an adequate solution. The central point to achieve detectors with minimal or nearly no dead volume is to take into account the connecting tubes. The results in this report show the advantage to transfer the solutions to the detection area in a straight short small bore capillary. Then the maintained laminar flow produces a negligiable dispersion. The quartz capillary detection cell in this report is 33 mm long and has a volume of 1.04 µl. By using a smaller ID column e.g. 0.05 mm the volume is 65 nl. The final solution is to locate the laser beam directly on the separation quartz capillary column, FIG. 9.

In the above there has consequently been described a method and a device for the detection of the presence of certain substances in a liquid by measuring the fluorescence radiation of the substances. The substances have been brought to fluorescence by means of a laser beam which is brought to illuminate the liquid over a minimum of volume at a flow point, where the liquid is flowing in a certain direction from a device for chromatographic separation. This device is represented in FIG. 1 by means of a unit 5 designated HPLC and a column 9, in which different substances are separated by means of their different physical and chemical properties and in this way the substances are brought to consecutively pass said flow point. This flow point can consequently be either a free falling liquid jet or a liquid channel in a capillary. Common is that the liquid passes the illuminated flow point in the form of a column with an accurately defined surface. The accurately defined surface is for example cylindrical with a highly even surface so that no disturbing refractive phenomenons are obtained. Essential is further that the laser beam is directed perpendicularly to the longitudinal direction of the liquid column, that is to say the flow direction of the liquid.

The device further includes a receiving unit 6 for the reception of the fluorescence radiation 3 emitted from the illuminated flow point. Essential is that the fluorescence radiation 3 is received in a direction outside the plane through the flow point which is perpendicular to the flow direction of the liquid. In this way scattering light and other nondesirable radiation is avoided caused by the radiation from the laser beam source, which is especially dominating in said direction and in this way the fluorescence radiation with a longer wavelength can be received with a minimum of disturbance level.

The above method and device has been described in connection with separation of a plurality of substances, but it is of course imaginable that the invention can be applied in such cases where the presence of a single substance will be detected.

REFERENCES

[1] R. P. W. Scott and P. Kucera, J. Chromatogr. 125 (1976) 251

[2] R. P. W. Scott and P. Kucera, J. Chromatogr. 169 (1979) 51

[3] D. Ishii, K. Asai, K. Hibi, T. Jonokuchi and M. Nagaya, J. Chromatogr. 144 (1977) 157

[4] Ishii and Takeuchi, J. Chrom. Sci. 18 (1980) 462

[5] J. H. Knox and M. T. Gilbert, J. Chromatogr. 186 (1979) 405

[6] G. J. Diebold and R. N. Zare, Science 196 (1979) 1444

[7] L. W. Hershberger, J. B. Callis and G. D. Christian, Anal. Chem. 51 (1979) 1444

[8] M. J. Sepaniak and E. S. Yeung, J. Chromatogr. 190 (1980) 377

[9] L. Johnson, B. Josefsson, P. Marstorp and G. Eklund Int. J. Enviro. Anal. Chem., 9 (1981) 7

[10] G. Taylor, Proc. R. Soc. (London) 219A (1953) 186

[11] E. S. Yeung and M. J. Sepaniak, Anal. Chem. 52 (1980) 1465A

[12] T. Tsuda and M. Novotny, Anal. Chem. 50 (1978) 271

[13] M. Krejci, T. Tesarik and J. Pajurek, J. Chromatogr. 191 (1980) 17.

We claim:

1. A method of detecting laser induced fluorescence in a liquid flowing in a chosen flow direction, to detect the occurrence of at least one chemical component in the liquid, comprising the steps of: directing a single light beam from a laser source substantially perpendicularly to the direction of flow to thereby cause molecules at one point of flow illuminated by the light beam to emit a fluorescent radiation; causing the liquid to pass said point in the form of a column with an accurately defined surface; and receiving the fluorescent radiation, by a receiving unit, in a direction deviating from the direction emanating from the illuminated flow point perpendicularly to the direction of flow.

2. A method according to claim 1, wherein, for detection at relatively low flow rates, said liquid column is a capillary consisting of quartz with a low inherent fluorescence, said capillary being highly transilluminable at said flow point.

3. A method according to claim 1, wherein, for flow rates from substantially 1 ml/min, said liquid column is a freely falling liquid jet with an accurately defined surface.

4. A method according to any one of claims 1 to 3, wherein said accurately defined surface is a cylinder mantle with a highly even surface structure.

5. An apparatus for detecting laser induced fluorescence in a liquid, comprising: means for causing said liquid to flow in a chosen flow direction; a laser source for directing a single light beam substantially perpendicularly to the direction of flow to thereby cause molecules at one point of flow illuminated by the light beam to emit a fluorescent radiation; means for causing the liquid to pass said point in the form of a column with an accurately defined surface; and means for receiving the fluorescent radiation, in a direction deviating from the direction emanating from the illuminated flow point perpendicularly to the direction of flow.

6. An apparatus according to claim 5, wherein said liquid column is a capillary consisting of quartz with a low inherent fluorescence, said capillary being highly transilluminable at said flow point.

7. An apparatus according to claim 5, wherein, for flow rates from substantially 1 ml/min, said liquid column is a freely falling liquid jet with an accurately defined surface.

8. An apparatus according to any one of claims 5 to 7, wherein said accurately defined surface is a cylinder mantle with a highly even surface structure.

9. An apparatus according to claim 5, comprising means for focusing the light beam substantially in the area of the illuminated flow point.

10. An apparatus according to claim 9, wherein said focusing means focuses the light beam in a point, positioned somewhat in front of the liquid column.

11. An apparatus according to claim 10, wherein said focusing means focuses the light beam substantially 15 mm in front of the liquid column.

* * * * *